United States Patent
Heumann

(10) Patent No.: US 6,783,751 B2
(45) Date of Patent: Aug. 31, 2004

(54) METHOD FOR LABELING BIOPOLYMERS USING ISOTOPES

(75) Inventor: Hermann Heumann, Grafelfing (DE)

(73) Assignee: Silantes GmbH, Munich (DE)

( * ) Notice: Subject to any disclaimer, the term of this patent is extended or adjusted under 35 U.S.C. 154(b) by 226 days.

(21) Appl. No.: 09/794,551

(22) Filed: Feb. 27, 2001

(65) Prior Publication Data

US 2003/0087234 A1 May 8, 2003

Related U.S. Application Data

(63) Continuation-in-part of application No. PCT/EP99/06154, filed on Aug. 21, 1999.

(30) Foreign Application Priority Data

Aug. 29, 1998 (DE) .......................... 198 39 491

(51) Int. Cl.[7] .......................... A61K 51/00; C12P 1/04; A61B 8/00
(52) U.S. Cl. .................. 424/1.11; 424/1.17; 424/1.18; 424/9.3; 435/170; 436/173; 436/804
(58) Field of Search ................................ 424/9.3, 1.11, 424/1.17, 1.65, 1.41, 9.1, 1.81; 435/170; 436/173, 804

(56) References Cited

PUBLICATIONS

Preparation of isotopically labeled ribonucleotides for multidimensional NMR spectroscopy RNA, 1992 Oxford University Press, Nucleic Acids Research, vol. 20, No. 17, p. 4515–4523.

XP–002128049, Structure of the recombination full–length hamster prion protein PrP (29–231): The N terminus is highly flexible, 13452–13456, 1997.

XP–002128050, enzymatic Synthesis of Region Specific Isotope–labeeled DNA Oligomers for NMR Analysis, American Chemical Society 1998,/ 120 607–608.

XP–002128053–Structural Change sof the *Escherichia coli* GroEL GroES chaperonins upon complex formation in solution, Academic Press, 1998.

XP–002128052, Improved large scale culture of Methylophilus methylotrophus for 13C/15N labelling and random fractional deuteration of ribonucleotides, Nucleic Acids Research, 1996, vol. 24 No. 23.

XP–002128054, 96139821 Medline Preparation of isotopically enriched RNAs for heteronuclear NMR, Batey R T; Battiste J L; Williamson J R, Dept. of Biology, Massachusetts Institute of Technology, Cambridge, 1995.

*Primary Examiner*—Michael G. Hartley
(74) *Attorney, Agent, or Firm*—Reed Smith LLP; Michael I. Wolfson

(57) ABSTRACT

The invention relates to a novel method for the in-vivo labeling of biopolymers such as proteins, nucleic acids, lipids, carbohydrates and biodegradable plastic using isotopes, especially stabile isotopes. The invention also relates to the use of chemolithotrophic bacteria for the in-vivo isotopic labeling of biopolymers. In particular, the invention relates to the use of $CO_2$-fixing bacteria, such as *Ralstonia eurtropha* and related methanogenic bacteria for the in-vivo isotopic labeling, especially for labeling using the stable isotope $^{13}C$ alone and in combination with other isotopes. In addition, the invention relates to the use of isotropically labeled biomolecules in therapeutic and diagnostic applications, especially in spectroscopic methods and generally as tracers.

13 Claims, 3 Drawing Sheets

METHOD FOR LABELING BIOPOLYMERS USING ISOTOPES

CROSS-REFERENCE TO RELATED APPLICATION

This application is a continuation-in-part of pending international application PCT/EP99/06514, filed on Aug. 21, 1999.

BACKGROUND OF THE INVENTION

The present invention concerns a new method for in vivo labeling of biopolymers, like proteins, nucleic acids, lipids, carbohydrates, and biodegradable plastic, with isotopes, especially stable isotopes and the use of chemolithotrophic bacteria for in vivo isotope labeling of biopolymers. The invention concerns in particular the use of $CO_2$-fixing bacteria, like Ralstonia eutropha and similar methanogenic bacteria for in vivo isotope labeling, especially for labeling with the stable isotope $^{3}C$ and the use of isotope-labeled biomolecules in therapeutic and diagnostic applications, especially in spectroscopy methods and generally as tracer compounds.

The deliberate use of biomolecules in diagnosis and therapy requires knowledge of the structure and dynamics of these molecules. This information can be obtained, for example, by using nuclear magnetic resonance (NMR). A prerequisite for efficient use of this method, however, is labeling of the biomolecules of interest with stable isotopes, so-called S isotopes, like $^{2}H$, $^{13}C$ and $^{15}N$.

Since S isotopes are not radioactive and, except for deuterium, are not toxic either, they have considerable diagnostic potential. S isotopes have already been successfully used in metabolic diagnosis. In addition to $^{2}H$, $^{13}C$ and $^{15}N$, the nuclei $^{1}H$, $^{7}Li$, $^{11}B$, $^{14}N$, $^{17}O$, $^{18}O$, $^{19}F$, $^{23}Na$, $^{29}Si$, $^{31}P$, $^{33}S$ and $^{77}Se$ have been used above all for NMR spectroscopy of organic compounds (cf., Vogel, H. J. (1989), Methods in Enzymology, Vol. 177, 263).

Use of S isotope-labeled substances, especially labeled amino acids, is discussed in imaging NMR spectroscopy, especially NMR microscopy. With further development of imaging NMR methods, the area of application of S isotope-labeled substances will expand and will not be restricted merely to the aforementioned S isotopes $^{2}H$, $^{1}C$ and $^{15}N$.

Thus far, complete S isotope-labeling of proteins and other biopolymers has generally occurred by in vivo labeling, i.e., organisms are cultured on isotope-labeled media and the desired protein or another component is then isolated from the labeled organisms.

The medium necessary for culturing, which generally consists of a carbon source, nitrogen source and salts, is more demanding and more cost-intensive, the more complex it is. This is particularly true of the carbon source. Since nutrient media for higher, i.e., eukaryotic, organisms are particularly complex, expression of S isotope-labeled eukaryotic proteins mostly occurs in recombinant fashion in bacteria, in most cases in Escherichia coli (see, for example, Donne, D. G. et al. (1997), Proc. Natl. Acad. Sci. USA 94, 13452–13457). These bacteria use glucose as inexpensive $^{13}C$-labeled carbon source. $^{13}C$-labeled methanol, which is relatively cheap, has been used as an alternative to culture Methylophilus methylotrophus (Batey, R. et al. (1995), Methods in Enzymology 261, 300–322). The most cost-effective carbon source is $^{13}C$-labeled $CO_2$. Green algae (for example, Chlorella vulgaris, Chlorella pyrenoidosa, Chlorella fusca or Scenedesmus obliquus) can fix carbon dioxide by photosynthetic reduction and therefore be completely labeled by feeding of $^{13}C$-labeled $CO_2$. The labeled algal hydrolyzate is then reused as carbon source to culture bacteria, especially E. coli.

The use of algal hydrolyzate instead of glucose is not only more economical, but in many cases also necessary for biological reasons. If foreign proteins are expressed in E. coli, the attainable cell density often drops, especially if minimal medium with glucose is used as carbon source. In many cases, the expression of a heterologous protein in E. coli is only possible by using algal hydrolyzate as C source; often at least the yield of heterologously expressed protein and thus the efficiency of the labeling method can be increased by supplying algal hydrolyzate.

Plasmid DNA from E. coli is manipulated for production of S isotope-labeled nucleic acids, especially DNA so that the desired nucleic acid sequence is displayed on the plasmid. An alternative method, which is obligatory for RNA and optional for DNA, is isolation of the entire RNA and DNA from labeled cells (E. coli or algae). After hydrolysis of DNA or RNA, isolation of nucleotides and phosphorylation to ribonucleoside triphosphates or deoxyribonucleoside triphosphates, new nucleic acids are synthesized in vitro with appropriate polymerases (Mer, G. and Chazin, W. J. (1998), J. Am. Chem. Soc. 120, 607–608).

Labeling with $^{13}C$ occurs in the prior art by means of complex and therefore costly carbon sources like $^{13}C$-glucose in the case of in vivo labeling of bacteria, like E. coli, or alternatively, using $^{13}C$-labeled carbon dioxide in the case of in vivo labeling of green algae and then supplying the $^{13}C$ labeled algal hydrolyzate as C source.

Labeling with $^{15}N$ generally occurs by using correspondingly labeled salts, labeling with $^{2}H$ by culturing in $D_2O$. Labeling with other isotopes occurs in similar fashion by metabolism of appropriately labeled substances.

In many cases labeling with several S isotopes is necessary. Double or multiple labeling can be achieved by a combination of different methods.

Radioactively-labeled biopolymers also find numerous applications in therapy and diagnosis. Thus, biomolecules labeled with radioactive isotopes are used, for example, as tracers or markers in testing metabolic and circulatory functions, in following and visually examining enrichment processes in tissues and organs, in radioimmunological and related in vitro assay methods as radiopharmaceuticals in nuclear medical in vivo diagnosis (for example, scintigraphy) and in autoradiography.

SUMMARY OF THE INVENTION

One task of the invention is to provide a new method for in vivo labeling of molecules a with isotopes.

A special task is to provide a process for in vivo labeling of biopolymers with stable isotopes, especially $^{13}C$, alone and in combination with other isotopes.

Another task consists of providing an in vivo labeling method that overcomes the drawbacks of the prior art methods and can be conducted more efficiently and more cost effectively in comparison with known methods.

These and other tasks are solved by the method according to the invention, which is based on the use of chemolithotrophic bacteria and is defined in the independent claims. Preferred variants of the invention are apparent from the subclaims.

In a particular variant of the method, in vivo labeling of biopolymers with isotopes, preferably stable isotopes, occurs by means of $CO_2$-fixing bacteria, labeling occurring in a preferred variant with stable and/or unstable carbon isotopes in methanogenic bacteria. Examples of methanogenic bacteria that are suitable for the in vivo labeling method according to the invention include *Acidovorax facilis, Alcaligenes ruhlandii, Alcaligenes latus,* Alcaligenes sp. 2625*, Ancylobacter aquaticus,* Ancylobacter sp. 1106–1108, 2456, 2457, 2666–2669*, Aquifex pyrophilus, Aquaspirillum autotrophicum, Azospirillum amazonense,* Azospirrillum sp. 1726, 1727*, Azospirilum lipoferum,* Azotobacter sp. 1721–1723*, Bacillus schlegelii, Bradyrhizobium japononicum, Bacillus tusciae, Calderobacterium hydrogenophilum,* Campylobacter sp. 806*, Derxia gummosa, Hydrogenophaga flava, Hydrogenobacter thermophilus, Hydrogenophaga palleronii, Hydrophaga pseudoflava, Hydrogenophaga taeniospiralis, Mycobacterium gordonae, Oligotropha carboxidovorans, Paracoccus denitrificans, Pseudomonas saccharophila, Pseudocardia autotrophica, Pseudocardia petroleophila, Pseudocardia saturnea, Ralstonia eutropha, Variovorax paradoxus, Xanthobacter agilis, Xanthobacter autotrophicus* and *Xanthobacter flavus.* Labeling occurs with particular preference in *Ralstonia eutropha* (previously also named *Alcaligines eutropha*).

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
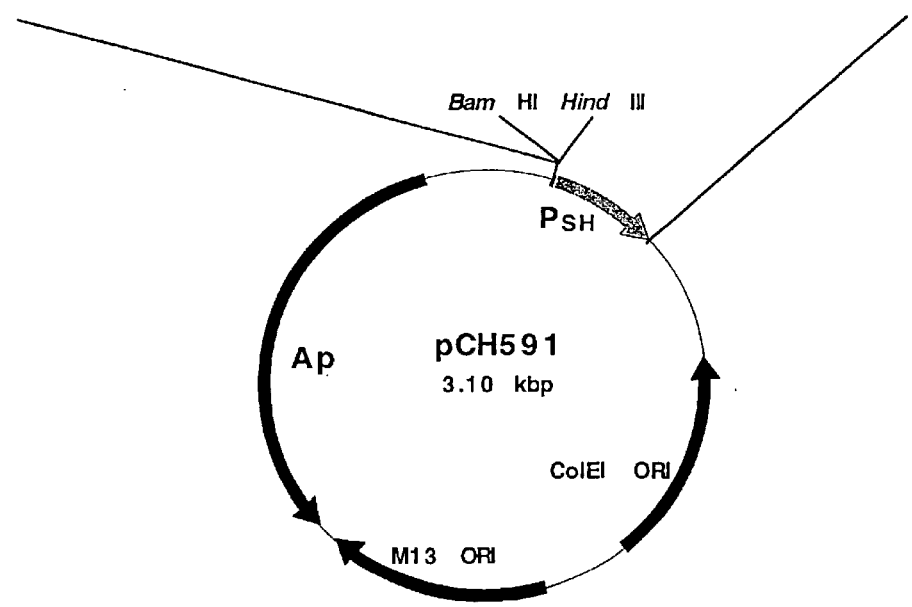
FIG. 1 is a showing of plasmid pCH591.

In contrast to green algae, which require electromagnetic radiation for fixation of carbon dioxide, chemolithotrophic bacteria use chemical redox reactions as energy source in which inorganic substrates are used as hydrogen donor. Carbon dioxide, which is fixed in the Calvin cycle, serves as carbon source for buildup of cell substance. Chemolithotropic bacteria are generally divided into the following subgroups: (i) nitrifying bacteria, in whose energy metabolism ammonium is oxidized to nitrite and then to nitrate or nitric acid, (ii) sulfur bacteria, which produce their metabolic energy by oxidation of one or more differently reduced or partially reduced sulfur compounds, (iii) iron- and manganese-oxidizing bacteria, and (iv) methanogenic bacteria, which include *Ralstonia eutropha* and the genus Hydrogenomonas which produce the required energy from reaction of oxygen and hydrogen, whose growth therefore requires the presence of hydrogen and oxygen. In contrast to most sulfur and nitrifying bacteria, the so-called methanogenic bacteria are only facultatively chemoautotrophic. This means that they grow heterotrophically in the presence of organic matter, like most bacteria and animals, and switch to the corresponding adequate type of metabolism in adaptation to the prevailing growth conditions. This offers the advantage that genetic manipulations in *Ralstonia eutropha* and other methanogenic bacteria can be conveniently conducted in the complex medium without $H_2$ and $O_2$.

The isotope labeling according to the invention is more cost-effective and less demanding than the methods of the prior art. In particular, the method according to the invention is characterized by the use of less costly and less complex growth media. In the case of labeling with C isotopes, for example, the stable $^{13}C$ isotope, the detour via culturing of green algae on appropriately labelled, for example, $^{13}C$-labeled carbon dioxide and production of algal hydrolyzate also drops out.

Moreover, $CO_2$-fixing bacteria, like *Ralstonia eutropha,* and other strains can also be used for production of isotope-labeled hydrolyzate in cases in which labeling *Escherichia coli* is inaccessible, as in green algae and their hydrolyzates.

Another advantage of the method according to the invention relative to the use of algae is the fact that *Ralstonia eutropha* and similar $CO_2$-fixing strains require no light for fermentation, grow more quickly than algae, reach higher cell densities, are less vulnerable to contamination and less sensitive overall than algae, so that culturing of the bacteria can generally occur much more easily and more cost effectively.

Another advantage of in vivo labeling in chemolithotrophic bacteria relative to *E. coli* consists of the fact that the concentration of carbon components during growth of $CO_2$-fixing bacteria is easier to monitor so that homogeneous labeling by the method according to the invention is easier to conduct than with *E. coli.*

The overall growth conditions during use of chemolithotrophic bacteria in comparison with *E. coli* are easier and more efficient to control because of the simpler growth media, since the concentration of components of the medium can be followed much more easily.

Additional advantages over known methods follow from the fact that the nucleic acid and protein fraction in the total biomass of *Ralstonia eutropha* and similar bacteria, is higher than in green algae, since green algae have a comparatively higher percentage of carbohydrates. Higher yields of isotope-labeled proteins or nucleic acids can be achieved on this account.

Moreover, the method according to the invention offers the advantage that a simple in vivo labeling of lipids in the future will also be possible in this way. Metabolic intermediates and secondary metabolites from chemolithotropic bacteria, especially $CO_2$-fixing bacteria and especially *Ralstonia eutropha,* can also be produced by the method according to the invention in isotope-labeled form. By using appropriate mutants, whose natural metabolic reactions are interrupted or destroyed, desired intermediates can be enriched. An example of an appropriate mutant suitable in the context of the method according to the invention is the PHB4 mutant, in which production of PHB (polyhydroxybutyrate) is disturbed (see, for example, Cook and Schlegel (1978), Arch. Microbiol. 119:231–235). The mutant PHB4 is deposited at the German Collection for Microorganisms and Cell Cultures (DSM Braunschweig) under deposit number DSM 541. Intermediates that are excreted or accumulated in mutant PHB4 include pyruvate, malate, citrate, fructose-6-phosphate and glucose-6-phosphate. In principle, any mutant is suitable in which the desired metabolites are excreted or enriched. Metabolism can therefore be deliberately or randomly disturbed so that new products form in the bacteria by enzymatic degradation or buildup.

In a particular variant, the method according to the invention for in vivo labeling of isotopes comprises the following steps:
 a) Culturing of chemolithotrophic bacteria, especially methanogenic bacteria in/on a nutrient medium containing at least one component labeled with an isotope,
 b) Harvesting of the bacteria and
 c) Isolation of the labeled biopolymer.

In a preferred variant, isolation of the labeled biopolymer includes $LaCl_3$ precipitation, as described, for example, in Abe, S. et al. (1987), Agric. Biol. Chem. 51(6):1729–1731.

Isolation of in vivo-labeled proteins from chemolithotropic bacteria preferably includes the steps:
 i) Opening of the cells by suspension of the harvested cells in an appropriate buffer, for example, an ordinary Tris/EDTA buffer, and addition of SDS,
 ii) Precipitation of nucleic acids and proteins with $LaCl_3$,
 iii) Elution of the proteins by a suspension in SDS-containing buffer solution and then centrifuging,
 iv) Precipitation of the proteins by ammonium sulfate precipitation.

Isolation of labeled nucleic acids preferably includes the steps:
 i) Opening of the cells by suspension of the harvested cells and an appropriate buffer, for example, an ordinary Tris/EDTA buffer, and addition of SDS,
 ii) Precipitation of nucleic acids and proteins with $LaCl_3$,
 iii) Elution of proteins by suspension in SDS-containing buffer solution and then centrifuging,
 iv) Dissolution of $LaCl_3$ pellets in EGTA-containing buffer solution (EGTA=ethylene glycol bis(β-aminoethyl ether)-N,N,N',N'-tetraacetic acid),
 v) Phenol extraction and then ethanol precipitation.

By using the method according to the invention, not only isotope-pure $^{13}C$-, $^{11}C$- and/or $^{14}C$-labeling can be carried out using $^{13}C$- or $^{11}C$-, $^{14}C$-labeled carbon dioxide as carbon source, but labeling with stable or unstable carbon isotopes can be simply combined with labeling of other isotopes, stable or unstable by choosing an appropriate nutrient medium containing the corresponding isotope. Thus, if exclusively $^{13}C$- or $^{11}C$-, $^{14}C$-labeled carbon dioxide is used as C source, when isotope-pure $^{13}C$- or $^{11}C$-, $^{14}C$-labeled cell mass of Ralstonia eutropha or other chemolithotrophic bacteria are to be obtained, $^{15}N_2$ or $^{15}N$-labeled salts can additionally be contained in the nutrient medium in order to obtain mixed labeling with isotope-pure $^{13}C$ and $^{15}N$.

Isotope-pure $^{13}C$- or $^{11}C$-, $^{14}C$-labeling can naturally also be combined with isotope-pure labeling with deuterium. In this case, $^2H$-labeling can occur by culturing Ralstonia eutropha or other chemolithotropic bacteria in $D_2O$ and/or by supply of $^2H_2$.

Moreover, mixed labeling with isotope-pure $^{13}C$ and $^{15}N$ and $^2H$ can be conducted, in which a percentage of $^2H$ of about 65–85% is preferred (cf., LeMaster, D. M. (1989), Methods in Enzymology, 177, 23 ff). Partial deuteration and therefore dilution of the spin is achieved from this content of deuterium.

The invention therefore concerns a special variant of in vitro labeling with a C isotope in combination with labeling with one or more additional isotopes, especially combined labeling with $^{13}C$ and $^{15}N$ and/or $^2H$.

Isotope-pure labeling with $^{15}N$ by merely using $^{15}N_2$- or $^{15}N$-labeled salts in the nutrient medium can naturally be conducted. The same applies for isotope-pure labeling exclusively with deuterium and mixed labeling with $^{15}N$ and $^2H$. The method according to the invention based on carbon dioxide-fixing bacteria can, in principle, be conducted with all stable or unstable isotopes in which stable or unstable C isotopes are offered, in particular, in the form of labeled carbon dioxide as C source in the nutrient medium.

The invention therefore also concerns the use of chemolithotrophic bacteria, especially methanogenic bacteria, for labeling of biopolymers with stable and/or unstable isotopes, especially with $^{13}C$, $^{11}C$, $^{14}C$, $^{15}N$, $^2H$ and $^{77}Se$, individually or in combination.

The invention also concerns the use of genetically engineered chemolithotrophic bacteria, preferably methanogenic bacteria, for expression of in vivo labeled proteins. Expression of proteins, preferably a heterologous protein, under control of a homologous promoter or heterologous promoter, can be involved (for example, the T7 system). The protein being labeled is preferably expressed in Ralstonia eutropha under control of a homologous promoter, for example, the SH (soluble hydrogenase) or MBH (membrane-bound hydrogenase) promoter from R. eutropha (see Schwartz, E. et al. (1998), Journal of Bacteriology, 3197–3204).

As another aspect, the present invention concerns the use of S isotope-labeled biomolecules according to the invention for NMR spectroscopy.

High resolution NMR spectroscopy in large molecules requires their labeling with stable isotopes, especially with the S isotopes $^2H$, $^{13}C$ and $^{15}N$. Use of isotope-labeled biomolecules according to the invention is therefore the so-called heteronuclear NMR technique.

The invention also concerns the use of biomolecules labeled according to the invention in imaging NMR spectroscopy in which the S isotope-labeled compounds are used as markers whose incorporation in the organism can be followed.

The invention also concerns the use of S isotope-labeled compounds in other NMR techniques, like solid NMR.

Additional use possibilities of the biopolymers labeled according to the invention are offered in conjunction with infrared and Raman spectroscopy. The vibration frequencies of molecular groups can be shifted by S isotope-labeling and therefore identified. If individual amino acids or individual nucleotides in a nucleic acid are deliberately S isotope-labeled in a protein, assertions concerning the conformation of this labeled molecule can be worked out with the spectroscopic methods.

Another area of use is mass spectrometry. The homogeneity of biomolecules can be analyzed via their mass distribution by means of mass spectrometry. The results of such mass spectrometric investigation are only unequivocal when the molecules are homogeneous with respect to their isotope composition. Since our environment consists of a mixture of isotopes, biomolecules are not isotope-pure either. For example, $^{12}C$ is mixed in our environment with a few percent of $^{13}C$. To be able to produce isotope-pure biomolecules, the organisms from which the desired biomolecules are isolated must be cultured beforehand on isotope-pure media.

S isotope-labeled biomolecules can also be used in neutron scattering. The isotopes $^1H$ and $^2H$ differ from each other in their spin. Since elastic scattering of neutrons occurs on the nuclear spin, $^2$H-labeled protein components can be distinguished from unlabeled components. The spatial arrangement of labeled components can therefore be determined by neutron radiation.

The aforementioned probes with which S isotope-labeled compounds can be identified or followed in an organism have enormous application potential in the life sciences, medicine, biology and biotechnology, since they (i) permit nondestructive analysis in most cases and (ii) the S isotope-labeling necessary for this purpose, with the exception of deuterium labeling, is not toxic. Use of these techniques, however, has thus far been limited by the availability of S isotope-labeled biopolymers, since labeling with ordinary methods is cost-intensive and the homogeneity of labeling required for most applications is connected with considerable technical and financial demands.

These drawbacks are overcome by using the method according to the patent, since the invention permits labeling at lower costs and higher quality, i.e., especially higher homogeneity, then ordinary methods.

A review of the mentioned spectroscopy techniques, especially NMR, mass, infrared and Raman spectroscopy can be found in Hesse, M., Meier, H. and Zeeh, B. in "Spectroscopic methods in organic chemistry", 5$^{th}$ edition, 1995, Georg Thieme Verlag, Stuttgart.

The invention also concerns the use of biomolecules labeled according to the invention with unstable isotopes, especially $^{11}$C or $^{14}$C in diagnostic and therapeutic applications, for example, as tracer compounds.

The invention will be better understood with references to the following examples. All percentages are set forth in molar percentages except when quantities by weight are indicated. These examples are presented for purposes of illustration only, and are not intended to be construed in a limiting sense.

EXAMPLES

Example 1

Culturing of R. eutropha

Strains of R. eutropha can be obtained from the German Collection of Microorganisms (DSM, Braunschweig) or the American Type Culture Collection (ATCC), for example, strain H16, which is deposited at DSM under deposit number DSM 428 and at the ATCC under number 17699.

R. eutropha can be cultured in standard media, for example, as described in Schwartz et al. (1998), supra, or Eberz, G. and Friedrich, B. (1991), Journal of Bacteriology 173, 1845–1854.

For chemolithotrophic growth of R. eutropha, the medium referred to as H-3 medium can be used, which is described in the "DSMZ catalog 1998" (German Collection of Microorganisms and Cell Cultures, Mascheroder Weg 1 B, 38124 Braunschweig).

H-3:

| | |
|---|---|
| $KH_2PO_4$ | 2.3 g |
| $Na_2HPO_4 \times 2H_2O$ | 2.9 g |
| $NH_4Cl$ | 1.0 g |
| $MgSO_4 \times 7H_2O$ | 0.5 g |
| $NaHCO_3$ | 0.5 g |
| $CaCl_2 \times 2H_2O$ | 0.01 g |

-continued

| | |
|---|---|
| $Fe(NH_4)$ citrate | 0.05 g |
| Trace element solution SL-6 | 5.0 mL |
| Distilled water | 980.0 mL |

Trace element solution SL-6:

| | |
|---|---|
| $ZnSO_4 \times 7H_2O$ | 0.1 g |
| $MnCl_2 \times 4H_2O$ | 0.03 g |
| $H_3BO_3$ | 0.3 g |
| $CoCl_2 \times 6H_2O$ | 0.2 g |
| $CuCl_2 \times 2H_2O$ | 0.01 g |
| $NiCl_2 \times 6H_2O$ | 0.02 g |
| $Na_2MoO_4 \times 2H_2O$ | 0.03 g |
| Distilled water | 1000 mL |

After adjustment of the pH value to 6.8, it was autoclaved at 121° C. for 15 minutes. $Fe(NH_4)$ citrate (0.05 g in 20 mL H20) is sterilized separately and then added to the medium. For chemolithotrophic growth of the bacteria, the culture is incubated under an atmosphere of 2% (v/v) $O_2$, 10% $CO_2$, 60% $H_2$ and 28% $N_2$ at a temperature of about 80° C. for about 4 hours. The atmosphere is produced by means of two communicating vessels (each about 10 L), one of which is filled with water (pH 3–5 in order to keep the solubility of $CO_2$ in water low). The different gases are forced into the water-filled supply vessel according to the above data. The volume of filled gases is obtained from the volumes of displaced water. The displaced water fills the second 10 L vessel. The water column produced in the second vessel serves to pressurize the gas mixture in the fermenter.

For the heterotrophic growth, the H-3 medium is supplemented by an appropriate carbon source (for example, 0.2% carbohydrate or 0.1% organic acid). $NH_4Cl$ is left out for growth in/on a nitrogen-free medium and the culture is incubated under an atmosphere of 2% (V/V) $O_2$, 10% $CO_2$, 10% $H_2$ and 78% $N_2$ or heterotrophically under 2% $O_2$ and 98% $N_2$.

During in vivo labeling, the corresponding components of the medium or atmosphere are replaced by correspondingly isotope-labeled compounds, for example, $CO_2$ is replaced with $^{13}CO_2$ during labeling with $^{13}$C. During labeling with $^{15}$N, either $N_2$ is replaced with $^{15}N_2$ or the N salts are replaced by $^{15}$N containing salts. During in vivo isotope labeling with $^2$H, $H_2O$ is replaced by $^2H_2O$ and $H_2$ by $^2H_2$.

Labeling with several isotopes occurs by a combination of the corresponding isotope-labeled components. Partial labeling occurs by changing the isotope concentration of the corresponding element.

Labeled starting substances, like $^{13}$C-labeled $CO_2$, can be obtained from Cambridge Isotope Laboratories (CIL), Massachusetts, USA.

Example 2

Isolation of Isotope-Labeled Proteins a) Opening of the Cells

After harvesting of the bacteria, 1.0 g cells are suspended in 10 mL TE buffer (100 mM Tris/EDTA, pH 7.5) and 1 mL 10% SDS (sodium dodecylsulfate) is added. The suspension is then incubated for 30 minutes at 37° C. and for another 30 minutes at 55° C. The solution is forced eight times through a syringe (diameter 0.1 mm) or in larger amounts through a French press. The solution is then centrifuged for 30 minutes at 18,000 rpm and the obtained supernatant transferred to a vessel. The bacterial pellet is taken up again in 10 mL TE buffer and 1 mL of 10% SDS is added. The suspension is then incubated again for 30 minutes at 37° C. and for another 30 minutes at 55° C. The solution is again forced through a syringe or French press and then centrifuged for 30 minutes at 18,000 rpm. The obtained supernatant is combined with the first supernatant so that the final volume is 20 mL.

b) Precipitation of DNA, RNA and Proteins 20 mL of 20 mM $LaCl_3$ is added dropwise during agitation to the supernatant from step a), then centrifuged for 20 minutes at 18,000 rpm. The pellet is washed with 10 mL $H_2O$ and then centrifuged again for 20 minutes at 18,000 rpm.

c) Elution of the Proteins 10 mL TE buffer containing 1% SDS is added to the pellet and the pellet is then thoroughly suspended. It is centrifuged at 18,000 rpm for 15 minutes and the supernatant transferred to a fresh vessel. 10 mL TE buffer containing 1% SDS is again added to the pellet and after resuspension of the pellet, the centrifuging step is repeated. The supernatant containing the proteins is combined with the first supernatant. The proteins can then be precipitated, for example, by ammonium sulfate precipitation, which can be caused by adding 7.0 g $(NH_4)_2SO_4$ (i.e., 3.5 g $(NH_4)_2SO_4$ per 10 mL of solution).

Example 3

Isolation of Isotope-Labeled DNA and RNA

The $LaCl_3$ pellet obtained in step b) in example 2 is taken up in 10 mL EGTA buffer (0.2M Tris base, 50 mM EGTA (ethylene glycol bis($\beta$-aminoethyl ether)-N,N,N',N'-tetraacetic acid), 50 mM KOH, 25 mM $Mg(OAc)_2$ and 10 mL of neutral phenol is added. The mixture is centrifuged in conjunction with deproteinization and DNA and RNA are precipitated from the aqueous phase with 2 volume units of ethanol.

For isolation of RNA, the DNA/RNA pellet is first taken up in 10 mL TE buffer. 300 $\mu$L of 1M $MgCl_2$ (up to 0.03M) and 1.0 mL 1M NaAc, pH 4.0 are then added. 10 mL phenol saturated with 0.1M NaAc, pH 4.0 is then added and the suspension centrifuged after thorough mixing. The aqueous phase is transferred to a new vessel and 10 mL of TE buffer is added again to the phenol phase. On conclusion of mixing and centrifuging, the aqueous phase is withdrawn and combined with the first aqueous phase. 2 mL 2M Tris base is added to the collected aqueous phases (20 mL volume) and the RNA precipitated with 2.5 to 3 volume units of ethanol.

For isolation of DNA 10 mL of 10 mM EDTA (ethylenediaminetetraacetic acid) and 1 mL 2M Tris base are added to the phenol phase. The suspension is then carefully mixed and heated at 80° C. for 5 minutes. Finally, the suspension is shaken for 5 minutes and then centrifuged.

The aqueous phase is removed and transferred to a fresh vessel. 10 mL of 10 mM EDTA and 1 mL of 2M Tris base are again added to the phenol phase. The suspension is then again carefully mixed and heated at 80° C. for 5 minutes. After shaking for 5 minutes and then centrifuging, the aqueous phase is combined with the first aqueous phase.

The DNA is precipitated from the collected aqueous phases (20 mL volume) with 2 volume units ethanol and 0.6 mL 3M NaAc, pH 4.8.

The yields of DNA, RNA and protein per g of cells of *Ralstonia eutropha* are as follows:

DNA: about 10.4 mg

RNA: about 11.4 mg

Protein: about 110 mg

Example 4

Figure 2:
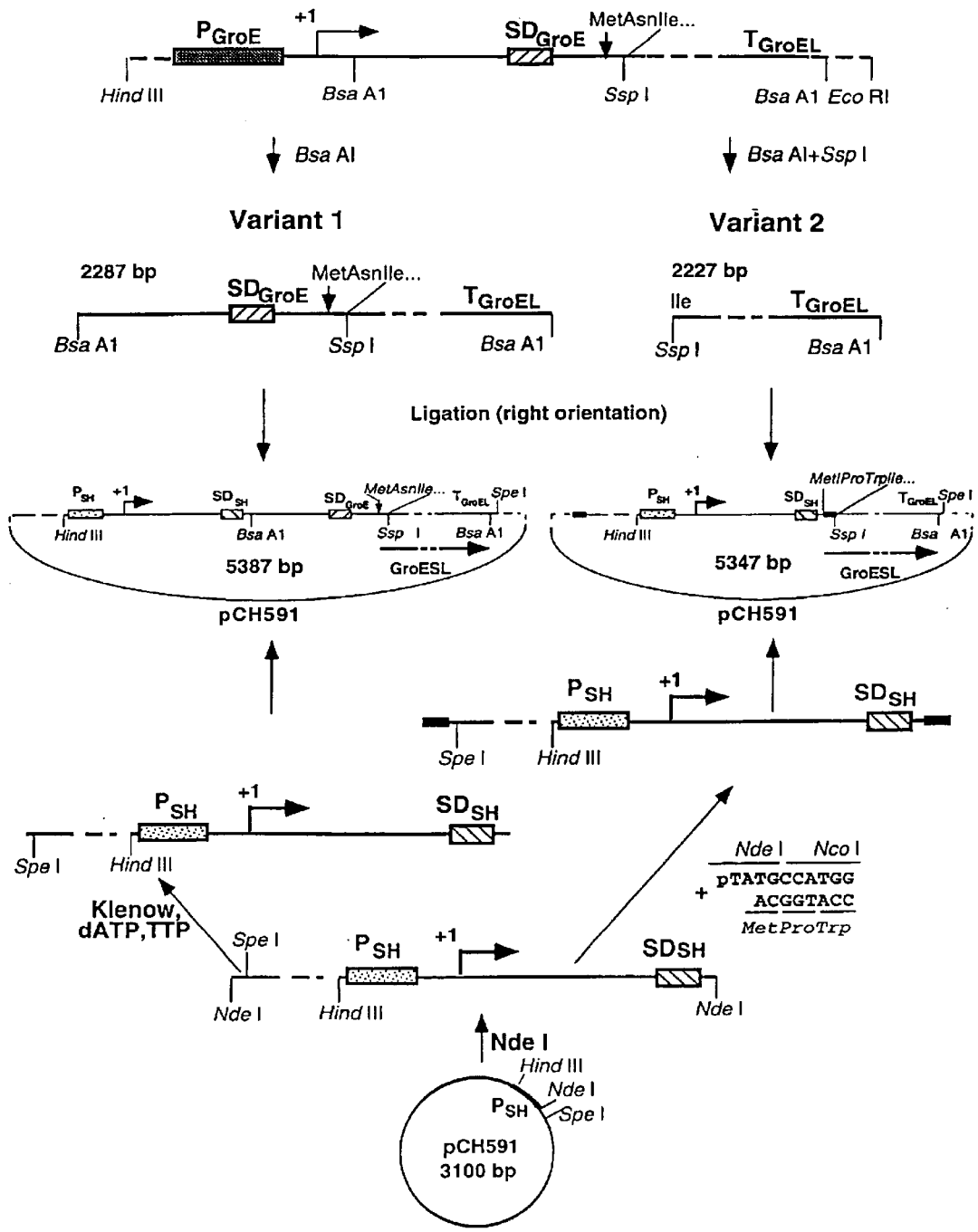
FIG. 2 shows the Hind III/Eco RI fragment of pOF 39 containing GroESL gene and the cloning into plasmid pCH591 of FIG. 1.

Preparation of a Genetically Altered Bacterium for Expression of Heterologous Proteins The vector plasmid pCH 591 (3.1 kb) based on Litmus 29, New England Biolabs, was used for cloning of the *E. coli* Chaperonin-GroESL gene. This plasmid carries an ampicillin resistance marker and a DNA fragment of *Ralstonia eutropha*, which includes the promoter region and the Shine-Dalgarno sequence of the soluble hydrogenase (soluble hydrogenase, SH) gene of *R. eutropha*, followed by a polylinker. Plasmid pCH 591 is shown in FIG. 1. The plasmid pOF 39 (R. Stegmann (1999), dissertation, Munich Technical University) served as source for the GroESL gene. As shown in FIG. 2, a 2.5 kb long Eco RI/Hind III fragment was isolated from pOF 39, which contains the GroESL gene. The Eco RI/Hind fragment isolated by agarose gel electrophoresis was then digested with the restriction enzyme Bsa AI in order to obtain blunt ends. This treatment led to elimination of the *E. coli* promoter and part of the transcription sequence, including the +1 transcription initiation nucleotide. The DNA region containing the Shine-Dalgarno sequence, as well as the initiation codon for the protein synthesis, were retained in the DNA region. The vector pCH 591 was treated with the restriction enzyme Nde I and the sticky ends filled up with Klenow DNA polymerase, followed by dephosphorylation using alkaline phosphatase. Finally, the treated vector was ligated with the Bsa AI fragment containing the GroESL gene using T4-DNA ligase and the supercomponent cells Solo Pack™ Gold cells (Stratagene) transformed with the ligation charge. The desired construct contains two Shine-Delgarno sequences, namely one from *E. coli* and another from *R. eutropha*. In a second cloning strategy for cloning of the GroESL gene, the Shine-Delgarno sequence of *E. coli* was eliminated, i.e., the desired constructs contained only the Shine-Delgarno sequence from *R. eutropha*. In the context of this strategy, the Eco RI/Hind III-GroESL fragment was treated with the restriction enzymes Bsa AI and SspI, in which the latter cuts the fragment at the site of the first two codons of the GroESL gene so that these two codons, as well as the *E. coli* Shine-Delgarno sequence, are eliminated. After treatment of vector pCH 591 with restriction enzyme Nde I, the 10-mer oligonucleotide depicted in FIG. 2 was ligated on the ends of the linearized DNA fragment. Not only is the Nde I-cleavage site reproduced by this oligonucleotide, but the oligonucleotide contains an Nco I cleavage site and codes for the amino acid Met and the two amino acids Pro and Trp (see FIG. 2). The obtained DNA fragment was ligated with the Bsa AI/SspI fragment containing the GroESL gene and the construct transformed to supercompetent Solopack Gold cells. The transformation was selected on LB medium containing 75 $\mu$g/mL ampicillin and isolated plasmid DNA was analyzed with respect to insertion of GroESL by means of a Hind III-Spe I restriction analysis in conjunction with the first cloning strategy and by Nde I or Nco I restriction digestion in conjunction with the second cloning strategy. The correct orientation of the GroESL fragment was then checked by appropriate restriction digestion. In addition, the desired fusion transitions were verified by sequencing. In the next step, the Hind III-Spe I fragment containing the *R. eutropha* promoter, Shine-Dalgarno sequence and GroEL/GroES gene is transformed in a wide host-range vector, in the present case the vector pEDY309 (21.2 kb) (derived from pEDY305, Schwartz et al. (1998), supra) and the obtained construct transformed in supercompetent Solo Pack™ Gold cells. The plasmid pEDY 309 contains a tetracycline-resistant gene, for which reason the transformants were cultivated on an LB medium containing 10 µg/mL tetracycline. The isolated plasmid DNA was analyzed by Hind III restriction digestion and the desired orientation additionally checked by sequence reactions and also PCR reactions. The desired DNA construct was transformed in *E. coli* S 17-1 and then conjugation of *R. eutropha* H16 cells carried out with the retransformed *E. coli* cells according to the conventional method. The conjugates were selected in the standard medium containing 0.4% succinate and 10 µL/mL tetracycline (see also Schwartz et al. (1998), supra).

Example 5

Figure 3:
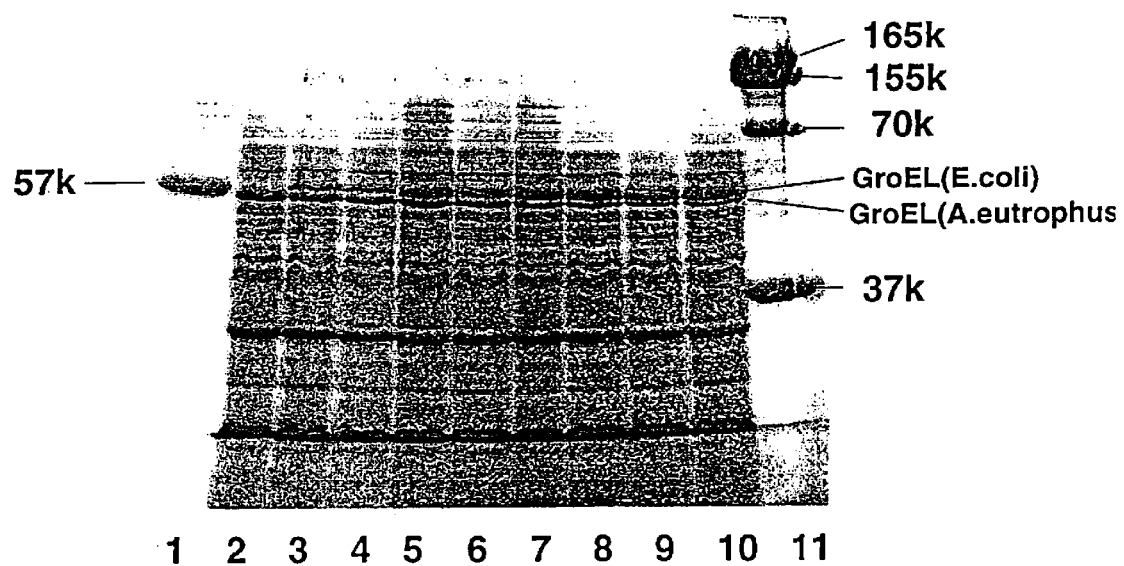
FIG. 3 is an SDS gel electrophoresis plot of the results of the expression of GroEl in *R. eutropha.* Track 1 and 11 shows reference proteins, GroEL from *E. coli* (track 1) and sub units of the RNA polymerase from *E. coli* (track 11) as molecular weight standard. Track 2 shows the protein pattern of *R. eutrophas* with the expression plasmid without GroEL/GroES gene, tracks 3 to 10 with GroEL/GroES gene. Tracks 3 and 4 show close 32 in clockwise orientation without (–) and in the presence of (+) tetracycline, respectively. Tracks 5 and 6 show clone 32 in counter clockwise orientation without (–) and in the present of (+) tetracycline, respectively. Tracks 7 and 8 shows close 9 in clockwise orientation without (–) and in the presence of (+) tetracycline, respectively. Tracks 9 and 10 shows clone 9 in counter clockwise orientation with (–) and in the presence of (+) tetracycline, respectively.

Expression of Heterologous Proteins in *R. eutropha* on the Example of *E. coli* Chaperonin GroEL/GroES Protein The recombinant *R. eutropha* cells from example 4 were cultured in a medium containing 0.2% fructose, 0.2% glycerol and 10 µg/mL tetracycline. After growth of the cells, the cells were harvested by centrifuging, resuspended in 100 µL of 10 mM HEPES, pH 7.5. 100 µL of 10% SDS was added and after heating for 2 minutes at 95° C. 20 µL of 0.1M $MgCl_2$ was added to the suspension. After removal of the DNA pellet by centrifuging, a 10 mL aliquot of the supernatant was analyzed in SDS gel electrophoresis. The result of expression of GroEL in *R. eutropha* is shown in the SDS gel depicted in FIG. 3. The cells were opened and the cell contents applied to the gel with further purification. Track 2 shows the protein pattern of *R. eutropha* with the expression plasmid without GroEL/GroES gene, tracks 3–10 with GroEL/GroES gene. Two clones (9 and 32) are shown, both in each orientation (direct clockwise and reverse counterclockwise) in the presence (+) and without (−) tetracycline. Tracks 1 and 11 show reference proteins, GroEL from *E. coli* (track 1) and subunits of the RNA polymerase from *E. coli* (track 10) as molecular weight standard. Comparison of the protein pattern in track 2 (expression without *E. coli* GroEL gene) with those in tracks 3 to 10 shows that a band with a molecular weight of 57 kDa is missing. This band corresponds to the *E. coli* GroEL protein. It can be concluded from the absence of the band in track 2 that *E. coli* GroEL was successfully expressed in *R. eutropha*. This could be confirmed by Western blotting. Expression of the heterologous GroEL protein is on the same order of magnitude as that of the homologous GroEL.

It will thus be seen that the objects set forth above, among those made apparent from the preceding description, are efficiently attained and, since certain changes may be made in the above methods without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A method for in vivo labeling of biopolymers by incorporating at least one isotope by the use of chemolithotrophic bacteria, including the stops of:
    a) culturing the bacteria in/on a medium containing at least one isotope and
    b) isolating the labeled polymers.

2. The method of claim 1, in which the bacteria is a $CO_2$-fixing bacterium.

3. The method of claim 1, in which the bacteria is a methanogenic bacterium.

4. The method of claim 1, in which the bacteria is *Ralstonia eutropha*.

5. The method of claim 1, in which the medium contain isotope-labeled carbon dioxide.

6. The method of claim 1, in which the isolation of the labeled biopolymers includes $LaCl_3$ precipitation.

7. The method of claim 1, in which the isotope is an S isotope.

8. The method of claim 1, in which the isotope is the isotope $^{13}C$.

9. The method of claim 8, including incorporating into the bacterium at least one additional stable isotope in addition to $^{13}C$.

10. The method of claim 9, in which the additional isotope is $^{15}N$ and/or $^{2}H$.

11. The method of claim 1, in which the isotope is an unstable isotope.

12. The method of claim 11, in which the isotope is $^{11}C$ and/or $^{14}C$.

13. The method of claim 1, in which the biopolymers are selected from the group of nucleic acids, lipids, carbohydrates, proteins, including heterologously expressed proteins, and mixtures thereof.

* * * * *